US010883150B2

(12) United States Patent
Yeber Ortiz et al.

(10) Patent No.: US 10,883,150 B2
(45) Date of Patent: Jan. 5, 2021

(54) **ISOLATED *PSEUDOMONAS AERUGINOSA* BACTERIAL STRAIN, NAMED CSMY-1, DEPOSITED UNDER ACCESSION NUMBER RGM2262, WHICH HAS THE CAPACITY TO DEGRADE POLLUTANTS PRESENT IN THE ENVIRONMENT, IN SOILS OR LIQUID INDUSTRIAL WASTE, AND ARSENIC-CONTAINING WASTE**

(71) Applicant: UNIVERSIDAD CATOLICA DE LA SANTISIMA CONCEPCION, Concepcion (CL)

(72) Inventors: Maria Cristina Yeber Ortiz, Concepcion (CL); Carolina Soto Espinoza, Concepcion (CL)

(73) Assignee: UNIVERSIDAD CATOLICA DE LA SANTISIMA CONCEPCION, Concepcion (CL)

( * ) Notice: Subject to any disclaimer, the term of this patent is extended or adjusted under 35 U.S.C. 154(b) by 62 days.

(21) Appl. No.: 16/070,682

(22) PCT Filed: Jan. 20, 2016

(86) PCT No.: PCT/IB2016/050279
§ 371 (c)(1),
(2) Date: Dec. 7, 2018

(87) PCT Pub. No.: WO2017/125784
PCT Pub. Date: Jul. 27, 2017

(65) Prior Publication Data
US 2019/0085419 A1    Mar. 21, 2019

(51) Int. Cl.
C12R 1/385 (2006.01)
B09C 1/10 (2006.01)
C02F 3/34 (2006.01)
C12N 1/22 (2006.01)

(52) U.S. Cl.
CPC ................ *C12R 1/385* (2013.01); *B09C 1/10* (2013.01); *C02F 3/34* (2013.01); *C12N 1/22* (2013.01)

(58) Field of Classification Search
CPC .. C12R 1/385; C12N 1/22; C02F 3/34; B09C 1/10
See application file for complete search history.

(56) References Cited

U.S. PATENT DOCUMENTS 4,199,444 A * 4/1980 Blair ........................ C02F 3/34
210/611

FOREIGN PATENT DOCUMENTS

CN    101638630 A    2/2010
CN    102296037 A    12/2011

OTHER PUBLICATIONS

Das et al., Genomics, 2015, vol. 105, p. 182-190, published online on Dec. 26, 2014.*
N. Bhatt, et al; Decolorization of diazo-dye reactive blue 172 by pseudomonas aeruginosa NBAR 12; Journal of basic microbiology; vol. 45; No. 6; 2005; pp. 407-418.
J. Arutchelvi, et al; Process optimization for the prosecution of rhamnolipid and formation of biofilm by Pseudomonas aeruginosa CPCL on polypropylene; Biochemical engineering journal; vol. 56; No. 1; 2011; pp. 37-45.
E. Pellizzari, et al; Degradacion de arsenico por Pseudomonas aeruginosa para bioremediacion de agua; Estudio Preliminar; Avances en Ciencias e Ingenieria; vol. 6; No. 1; 2015; pp. 1-5.
K. Krumova, et al; Isolation and identification of Arsenic-Transforming bacteria from arsenic contaminated sites in Bulgaria; Biotechnology and Biotechnological Equipment; vol. 22; No. 2; 2008; pp. 721-728.
International Search Report dated Oct. 13, 2016 for PCT/IB2016/050279 and English translation.

* cited by examiner

*Primary Examiner* — Kade Ariani
(74) *Attorney, Agent, or Firm* — Lucas & Mercanti, LLP

(57) ABSTRACT

The invention relates to an isolated bacterial strain of *Pseudomonas aeruginosa* species, referred to as *Pseudomonas aeruginosa* CSMY-1, deposited in the Microbial Genetic Resources Bank of the Chilean Collection of Microbial Genetic Resources (CChRGM), under accession number RGM2262, on Aug. 7, 2015, which is a facultative strain that can remove chemical components having characteristics that pollute natural or industrial effluents or soils by degrading compounds. The invention also relates to a method for the pollutant bioremediation of a contaminated environments, comprising: a) adding bacteria *Pseudomonas aeruginosa* CSMY-1 in the form of a biofilm to said contaminated environment; and b) incubating said bacteria *Pseudomonas aeruginosa* CSMY-1 in the form of a biofilm in said environment.

10 Claims, 8 Drawing Sheets

(A)

(B)

(A)

(B)

ISOLATED *PSEUDOMONAS AERUGINOSA* BACTERIAL STRAIN, NAMED CSMY-1, DEPOSITED UNDER ACCESSION NUMBER RGM2262, WHICH HAS THE CAPACITY TO DEGRADE POLLUTANTS PRESENT IN THE ENVIRONMENT, IN SOILS OR LIQUID INDUSTRIAL WASTE, AND ARSENIC-CONTAINING WASTE

CROSS REFERENCE TO RELATED APPLICATION

This Application is a 371 of PCT/IB2016/050279 filed on Jan. 20, 2016, which is incorporated herein by reference.

FIELD OF THE INVENTION

The present invention relates to an isolated bacterium *Pseudomonas aeruginosa*, named CSMY-1, deposited under accession number RGM2262 in the Microbial Genetic Resources Bank (Banco de Recursos Genéticos Microbianos) of the Chilean Collection of Microbial Genetic Resources (Colección Chilena de Recursos Genéticos Microbianos, CChRGM, por sus siglas en inglés) in its status as International Depositary Authority (IDA), dated Aug. 7, 2015. This new strain is capable to degrade pollutants in the environment, specifically in industrial soils or liquid industrial waste, such as liquid industrial waste containing dyes from textile industry; lignin-containing waste from cellulose industry; petroleum waste and its derivatives from petroleum industry, and heavy metals and arsenic-containing waste. This process to degrade polluting compounds, both in the environment and in living beings through a bacterium, *Pseudomona aeruginosa* CSMY-1 in this case, is called bioremediation.

The invention also relates to a method of bioremediation of industrial soils or liquid industrial waste contaminated with dyes, lignin, petroleum and its derivatives, and arsenic-containing waste using said *Pseudomonas aeruginosa* CSMY-1 strain RGM2262.

STATE OF THE ART

In recent decades, the release of pollutants to the environment, mainly produced as a result of industrial development, has far exceeded natural mechanisms of recycling and self-purification of the receiving ecosystems.

Physical and a good part of chemical treatments are based on transferring pollution between gaseous, liquid and solid media, however through bioremediation little pollution is transferred from one medium to another. Currently, the majority of industrial effluent treatments consider a filtration and/or coagulation stage and few consider treatments with aeration lagoons where the liquid industrial waste remain a long period of time in recirculation without changing their "price-evacuation" characteristics, i.e., the ratio between invested cost versus system efficiency, which does not improve. Bioremediation is a minimally invasive technology and generally does not require structural or mechanical components that pose a threat to the environment. Comparatively, it is economically viable and being a natural process is usually accepted by public opinion.

Management of bioremediation using microorganisms in a controlled system effectively manages to occupy organic matter carbon present in an effluent as an energy source for its growth. On the other hand, removal of organic and inorganic compounds is over 80% without generation of sludge.

Unfortunately, incomplete biodegradation creates unacceptable metabolic intermediates, which have a similar or even higher pollutant power than the starting product and some polluting compounds are so resistant that can even inhibit bioremediation.

ECF bleaching effluent, for example, contains mainly organic matter derived from lignin, giving it a brown color which when poured into water bodies blocks the passage of light, decreasing the photosynthetic capacity and causing eutrophication; whereby there is a need for these effluents to be treated prior to discharge.

Dark color of the effluent disappears when lignin is removed, so the passage of light in aquatic systems is no longer blocked and neither is the photosynthetic capacity of the aquatic flora. On the other hand, by reducing phenols, which are a fundamental part of lignin structure, the risk of causing damage to the aquatic ecosystem and destroying important natural resources decreases.

It is the same for arsenic. Arsenic is a natural pollutant of aquifers and arsenic removal from polluted water is generally carried out by different procedures including, but not limited to, coagulation-chemical sedimentation, oxidation-reduction, adsorption and ion exchange. The problem is that these methods have several disadvantages such as high cost of implementation and also the generation of secondary residues.

In the case of dyes from textile industry, these dyes are not usually toxic, but are poorly biodegradable. Only 20%-30% of the color of the tributary is likely to be removed. In addition, dyes tend to show in water even at very low concentrations, so removal processes is required to have a very high removal yield Various technologies based on physicochemical treatments have traditionally been applied to remove textile effluent color. However, there are other possibilities that are opening up depending on the type of dye to be removed. These technologies include, but are not limited to, coagulation-flocculation, Fenton process, ozonization, membrane technology, adsorption, biotechnological processes.

Regarding the study of products and processes that accelerate degradation of pollutants present in the environment and which are similar to the present technology, we have the following documents:

Patent application ES 2329643, describes a microorganism *Pseudomona* sp. Pme 707 (CECT 7314) which is characterized by its capacity of degrading aqueous-oily fraction of oily residues from food and hotel industry, due to its capacity to produce substances that stimulate quorum sensing mediated microbial activity of different bacteria helping to degrade residual components of waters and oily effluents. However, ES 2329643 does not describe the bacterial strain or the bioremediation method steps described by the present application.

Spanish patent application, ES 2523412, describes a method for reducing COD from residual metal working fluids, comprising contacting the metal working fluid with a biofilm, wherein the biofilm has at least four members selected from at least one of each of *Agrobacterium* spp., *Comamonas* spp., *Methylobacterium* spp., and *Microbacterium* spp. However, ES 2523412 does not describe the bacterial strain or the bioremediation method described in the present application. In addition, the present invention relates to only one bacterial strain and not to a bacterial consortium. On the other hand, ES 2523412 describes a treatment for waste metal residues and do not disclose dyes, lignin or arsenic as does the present invention.

Therefore, seeking to reduce the release of pollutants, there is a need to search for processes which can accelerate degradation of pollutants present in the environment, specifically from industrial soils or liquid industrial waste, such as liquid industrial waste containing dyes from textile industry; lignin-containing waste from cellulose industry; petroleum waste and its derivatives from petroleum industry, and As (III)-containing waste. So the harmful effects produced by them on ecosystems and human health will be progressively reduced.

DESCRIPTION OF THE INVENTION

Figure 1:
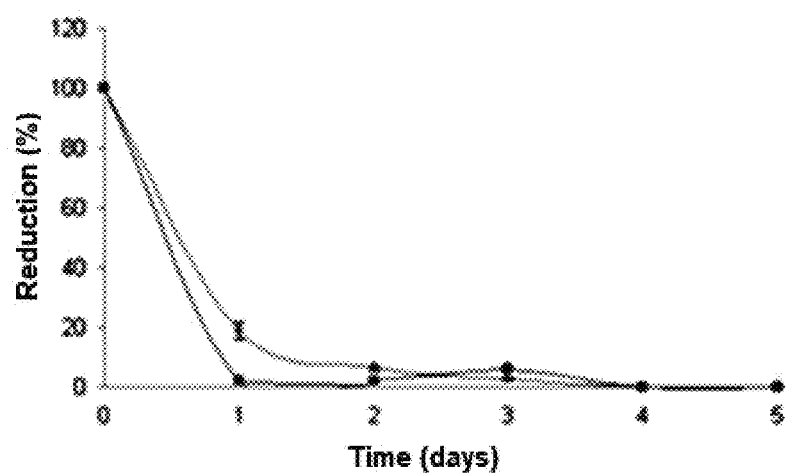
FIG. 1: It shows color removal of Kraft Lignin by bacterium *Pseudomonas aeruginosa* CSMY-1 over time. (■) Corresponds bacteria removal in biofilm. (♦) Corresponds to bacteria removal without biofilm (pelagic form).

The present invention relates to an isolated bacterial strain, *Pseudomonas aeruginosa*, named CSMY-1, which is able to remove chemical polluting components from industrial, natural effluents or soils through the degradation of the compounds thus minimizing their consequences, both in the environment and in living beings, a process called bioremediation.

Said bacterial bioremediator strain, *Pseudomonas aeruginosa* CSMY-1, was deposited under accession number RGM2262 in the Microbial Genetic Resources Bank of the Chilean Collection of Microbial Genetic Resources (CChRGM) in its status as International Depository Authority (IDA), dated Aug. 7, 2015, under the Budapest Treaty. This strain is an opportunistic pathogenic bacterium in humans and plants, which even is described as an aerobic bacterium, also supports anaerobic conditions effectively, i.e., a facultative bacterium. Degradation capacity thereof has been proved in cellulose and commercial lignin effluents and its capacity to remove textile compounds, dyes, phenols, arsenic (III) and petroleum has also been demonstrated by contacting them with the bacterial strain. Additionally, the strain of the present invention forms biofilms, which gives the bacteria comprised therein a greater resistance to force of the tributary where they are deposited.

To form the biofilm, the bacterium *Pseudomonas aeruginosa* CSMY-1 is incubated in a culture medium, such as, soybean trypticases broth, together with a polyethylene sheet, for a period of time ranging from 3 to 15 days at temperature from 25° C. to 40° C. This biofilm is resistant since the bacteria does not detach when is used, even when it is washed with distilled water, remaining intact.

Furthermore, the present invention describes a method for removal of pollutants. The method consisting of forming a bacterium *Pseudomonas aeruginosa* CSMY-1 biofilm; and exposing said biofilm to soils and liquid industrial waste from textile industry containing dyes; from cellulose industry containing lignin; from petroleum industry containing petroleum and its derivatives, and from waste containing As (III).

The method of removal of pollutants from contaminated environments, or bioremediation, includes the steps of:

a) adding bacterium *Pseudomonas aeruginosa* CSMY-1 in biofilm form to said polluted environment, wherein said *Pseudomonas aeruginosa* strain CSMY-1, RGM2262, is capable to remove pollutants;

b) incubating said bacterium *Pseudomonas aeruginosa* CSMY-1 in biofilm form in said environment during a period of time from 5 to 10 days, from 20° C.-40° C. at a pH range from 4 to 11 to allow the removal of contaminants.

In a specific embodiment of the invention, the bacterial strain is grown in polyethylene sheets to form a biofilm, at an initial concentration from 0.01 to 10 g/L of the strain.

In a specific embodiment of the invention, the pollutants removed by bacterium *Pseudomonas aeruginosa* CSMY-1 in biofilm form are:

1. pollutants from the textile industry, containing dyes such as Black Reactive 5, RD K4-BL and CBY 3G-P;
2. pollutants from the cellulose industry containing lignin in the waste, such as, for example, kraft cellulose effluent;
3. pollutants from the petroleum industry having petroleum waste and its derivatives, such as hydrocarbons, and
4. arsenic (III)-containing waste.

In another specific embodiment, the method of removing pollutants from contaminated environments comprises adding glucose at a concentration from 0.1 to 0.5 m g/L.

In another specific embodiment, the method of removing pollutants from contaminated environments comprises adding a trace metal solution, wherein trace metals used are Co, Ni, Mg, Fe, which are in stock solution and are used from 10 to 200 µL.

In another specific embodiment, the method of removing pollutants from contaminated environments comprises adding iron at a concentration from 0.05 to 0.1 mg/L.

EXAMPLES

Example 1

Method for Isolating and Modifying *Pseudomonas aeruginosa* CSMY-1

*P. aeruginosa* CSMY-1, was isolated from pond water contaminated with traces of diesel, at the Universidad Católica de la Santísima Concepción, campus San Andrés.

A sample of 20 mL of puddle water was extracted and plated using the serial dilution technique and plate count on King A agar base, which is a selective culture medium for *Pseudomonas*, wherein *P. aeruginosa* colonies grow bluish green. A colony of *Pseudomonas* was obtained, which was then transferred to King A agar to multiply. Some of them were then selected for oxidase assay to assess the strain for hydrogen peroxide production caused by the presence of cytochrome oxidase. For this, a bacteria sample is placed on a disc impregnated with N,N,N,N-Tetramethyl-p-phenylenediamine (or TMFD) or N,N-Dimethyl-p-phenylenediamine (or DMFD), both indicators will show a color change from blue to red and even black, when the test is positive. The colonies were oxidase positive, and the API® 20E Profile Analytical Index test was used for their identification, the test consists of a battery of substrates to grown the strains and see the characteristics that define the species. The oxidase assay and the API 20E test confirmed that the isolated bacterium was *Pseudomonas aeruginosa*.

Example 2

Degradation of Kraft Lignin by Bacteria *Pseudomona aeruginosa* CSMY-1 in a Continuous Flow Pilot Bioreactor A pilot bioreactor was used to assess kraft lignin degradation by bacterium *Pseudomonas aeruginosa* CSMY-1 biofilm. Bioreactor length is 35 cm, diameter 6.5 cm and a capacity 1.2 liters, its flow is 606.63 mL*$m^{-1}$. The bacteria are found therein on a polyethylene sheet having 21.5 cm×2 cm. The process of bacterial biofilm formation requires the bacterium to be incubated at a concentration of 1 g/L in trypticase soy broth together with the polyethylene sheet for a period of 7 days at a temperature of 37° C., so the bacteria started to secret glycocalyx thus forming the biofilm.

About 3 liters of kraft lignin solution was used for recirculation in the reactor, kraft lignin solution was recirculated for 6 hours driven by a peristaltic Master Flex L/S 7754-95 pump, the optimal pump speed was 2 rpm for avoiding bacteria detachment from biofilm.

For testing effectiveness of the bacteria in pelagic form (without biofilm), 100 ml of 100 ppm kraft lignin solution were prepared, it was inoculated with 500 µL of *Pseudomonas aeruginosa* CSMY-1, at concentration of $10^8$ cel*m/L, and incubated at 37° C. for a period of 120 hours, at pH 8. Five mL were extracted each 24 hours to analyze kraft lignin and kraft cellulose removal and 500 µL were extracted each 24 to assess bacterial growth from the serial dilution method and plate count on trypticase agar.

Figure 2:
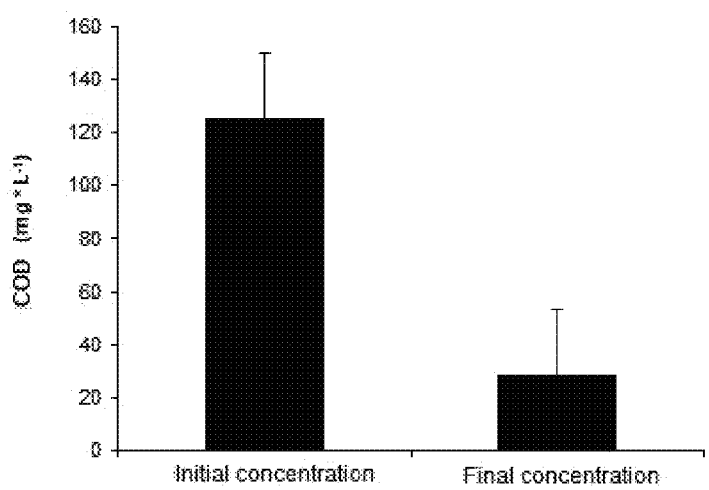
FIG. 2: It shows COD (mgO$_2$/L) before and after the treatment of Kraft lignin with *Pseudomonas aeruginosa* CSMY-1 in a pilot continuous flow reactor.
Figure 3:
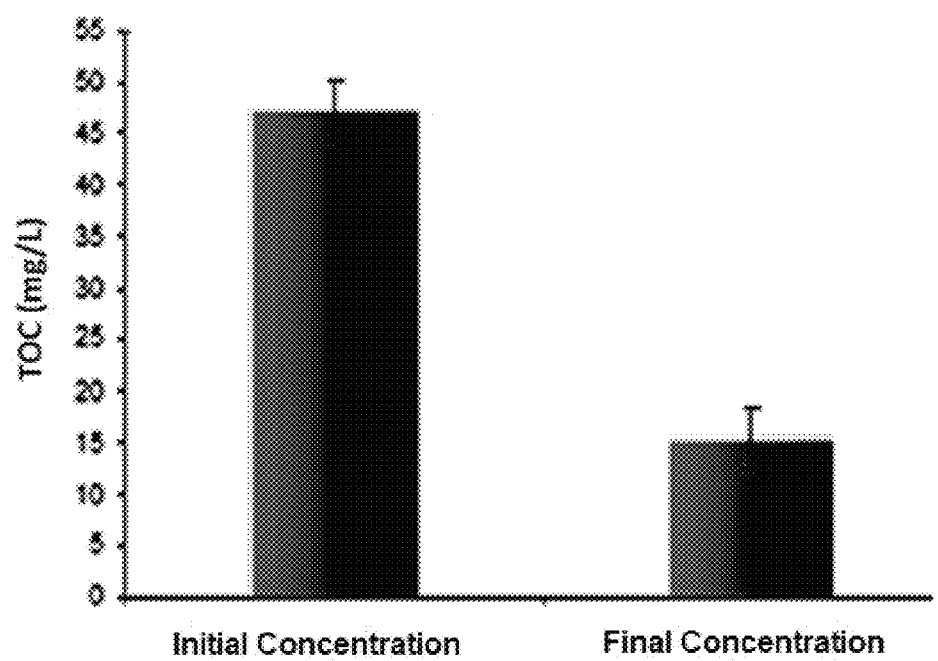
FIG. 3: It shows TOC (mgO$_2$/L) before and after treatment of Kraft lignin with *Pseudomonas aeruginosa* CSMY-1 in continuous flow pilot reactor.

As a result, it was observed an 80% color removal from Kraft lignin by biofilm bacteria within 24 h, achieving 97% on day 5 (FIG. 1). The difference is that the effect of the biofilm is observed on the first day, with about 97%. On the other hand, without biofilm, a similar effect is observed after 4 days. Chemical Oxygen Demand reduction reached 78.6% (FIG. 2), agreeing with total organic carbon (TOC) reduction (FIG. 3) showing that bacteria is efficiently consuming organic matter.

Example 3

Degradation of Pollutants from a Kraft Cellulose Effluent by Bacterium P *Pseudomonas aeruginosa* CSMY-1 in a Continuous Flow Pilot Bioreactor The same previous system (continuous flow bioreactor) was used to degrade a kraft cellulose effluent from the first stage of a (ECF) bleaching sequence extraction of a cellulose plant, since this stage is the one that contributes with the higher organic load and color to the total effluent.

Glucose was added in this treatment with bacterium CSMY-1 biofilms, to observe the effect of an additional nutrient on degradation efficiency. Sugar is one of the fundamental components for the bacterium to form glycocalyx, so the availability of sugar in the medium favors biofilm formation; as well it provides additional energy for growing, achieving over 90% of phenolic compound degradation in the effluent during an optimized period of 10 days.

Figure 4:
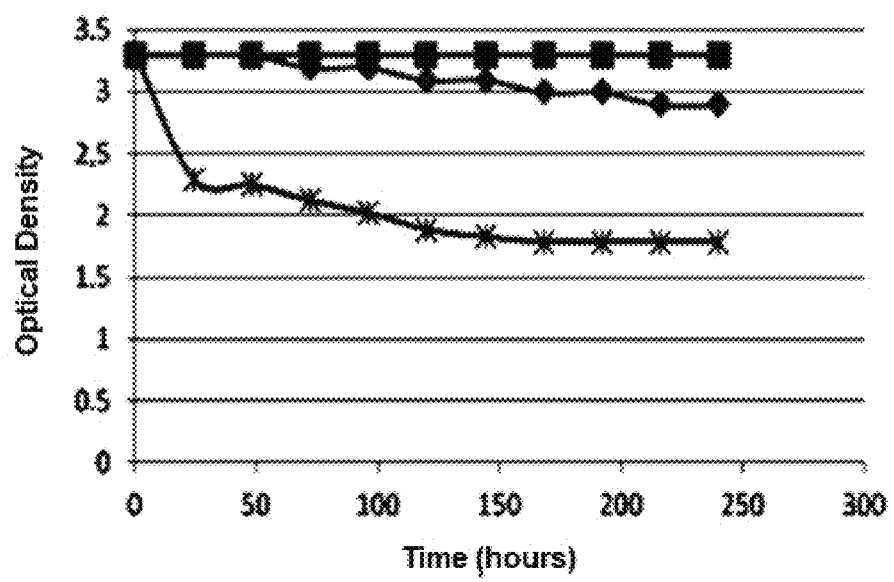
FIG. 4: Kinetics of phenol removal by *P. aeruginosa* CSMY-1 and *C. cladosporoides*. (A) corresponds to the removal without addition of glucose, wherein (■) represents the untreated liquid industrial waste sample; (♦) represents the sample treated with *C. cladosporoides* and (*) represents the sample treated with *Pseudomonas aeruginosa* CSMY-1. (B) corresponds to removal with addition of glucose, wherein (■) represents the untreated liquid industrial waste sample; (▲) represents the sample treated with *C. cladosporoides* and (*) represents the sample treated with *Pseudomonas aeruginosa* CSMY-1.
Figure 4:
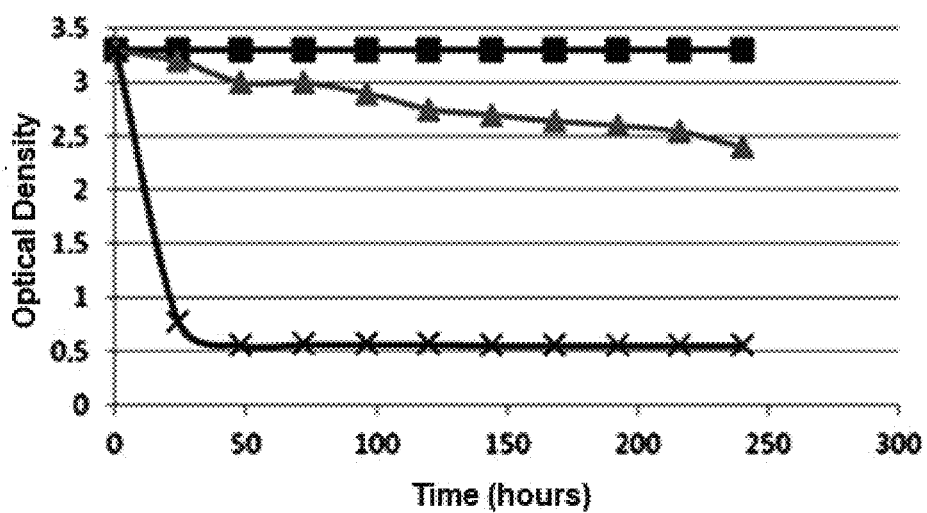
Figure 5:
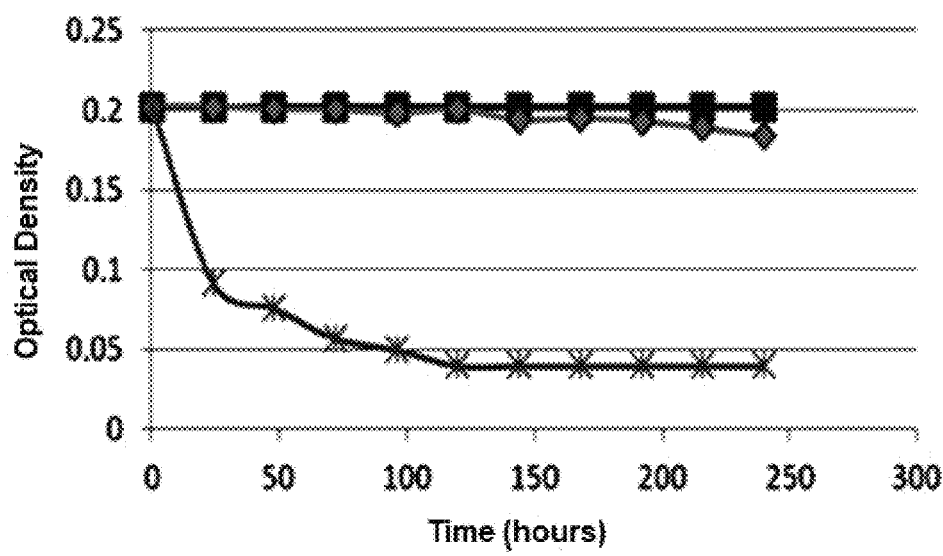
FIG. 5: It shows kinetics of color removal by *P. aeruginosa* CSMY-1 and *C. cladosporoides*. (A) corresponds to the removal without addition of glucose, wherein (■) represents the untreated liquid industrial waste sample; (♦) represents the sample treated with *C. cladosporoides* and (*) represents the sample treated with *Pseudomonas aeruginosa* CSMY-1. (B) corresponds to removal with addition of glucose, wherein (■) represents the untreated liquid industrial waste sample; (▲) represents the sample treated with *C. cladosporoides* and (X) represents the sample treated with *Pseudomonas aeruginosa* CSMY-1.
Figure 5:
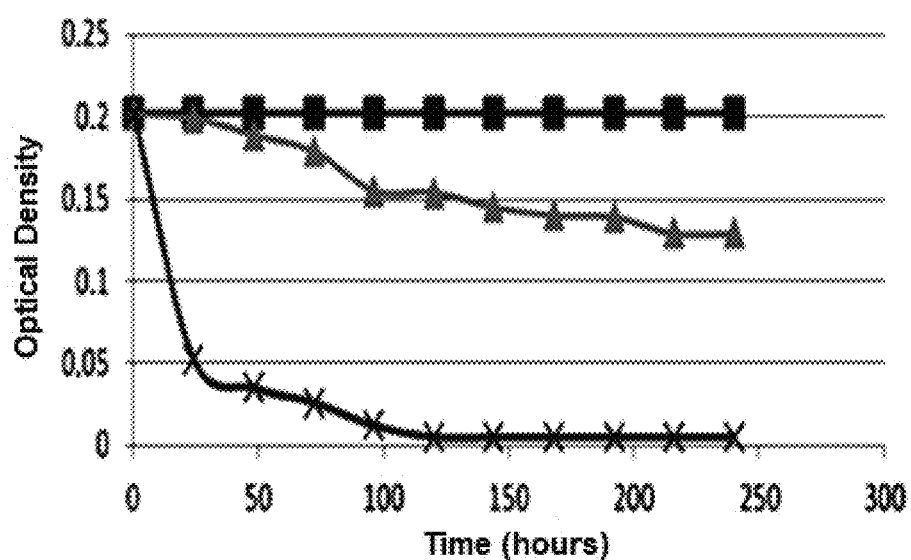
Figure 6:
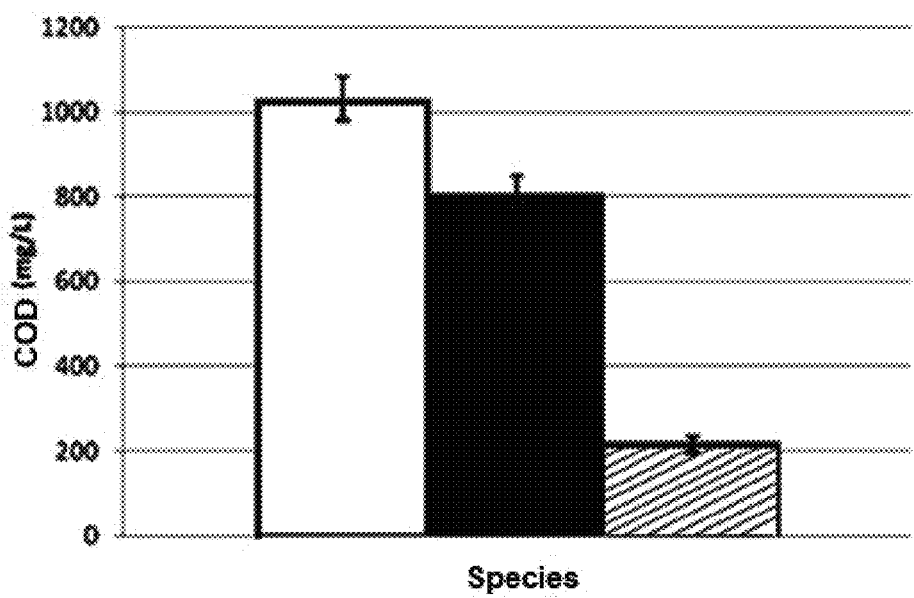
FIG. 6: It shows COD (mg/L) in the degradation of pollutants from a kraft cellulose effluent by bacterium *Pseudomonas aeruginosa* CSMY-1 in a continuous flow pilot bioreactor. White, Initial industrial liquid waste; black, *C. cladosporoides*; Striped, *Pseudomonas aeruginosa* CSMY-1.

The results of the glucose addition method showed that *Pseudomonas aeruginosa* CSMY-1 was efficient at removing 83.06% of total phenols (FIG. 4 B), 97.57% of color (FIG. 5B) and 78.4% of COD at pH 7 (FIG. 6), liquid industrial waste dilution factor of 70%, 2.5 g/L and 10 g/L glucose. A comparison was made using *C. cladosporoides* fungus achieving a removal of only 30.30% of total phenols, 41.08% of color and 21.7% of COD.

The use of glucose as a carbon source for both *C. cladosporoides* and *Pseudomonas aeruginosa* CSMY-1, as well as for a better biofilm structure formation, favored the increase of biomass for both species, which was directly associated with a greater removal of color and phenol, which are components difficult to degrade in natural environments.

Example 4

Removal of Arsenic (III) by *Pseudomonas aeruginosa* CSMY-1 in Biofilm Form in a Glucose and Trace Metals Enriched Medium 250 mL of As (III) solution at concentrations of 0.05 mg/L, 0.1 mg/L, 1 mg/L, 2 mg/L and 3 mg/L were prepared in duplicate and 14 strips of biofilm bacteria were added at each concentration. Treatments were incubated at 37° C. for 120 h. As (III) removal kinetics was monitored without adding glucose or trace metals and adding these at 24 h of incubation. In each case, a sample was taken every 24 h to assess residual arsenic.

Figure 7:
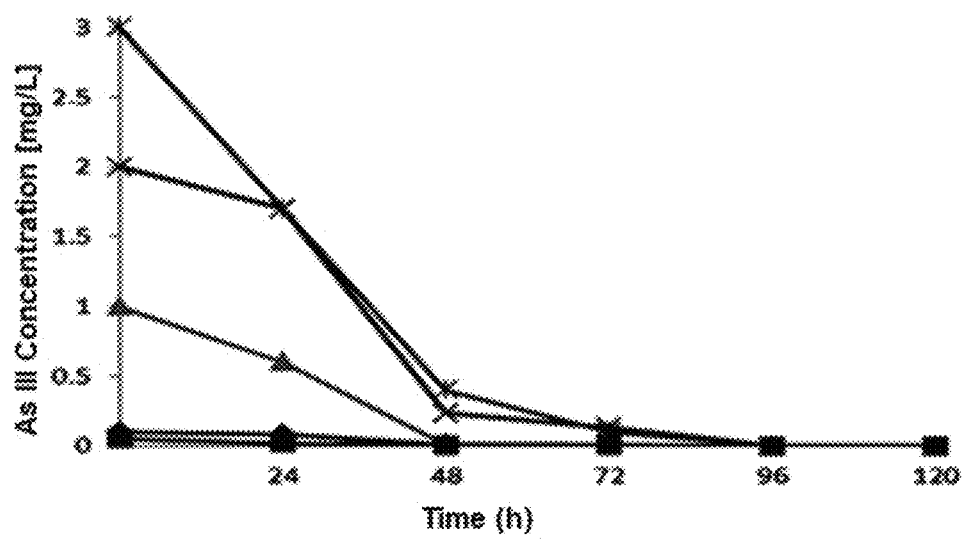
FIG. 7: It shows removal of Arsenic (III) by biofilms of *P. aeruginosa* CSMY-1 in a trace metal-enriched medium. Metals are added at 24 hours of incubation, causing a visible effect at 48 hours. As (III) is found in the following concentrations (■) 0.05 mg/L; (♦) 0.1 mg/L; (▲) 1 mg/L; (X) 2 mg/L; (*) 3 mg/L.
Figure 8:
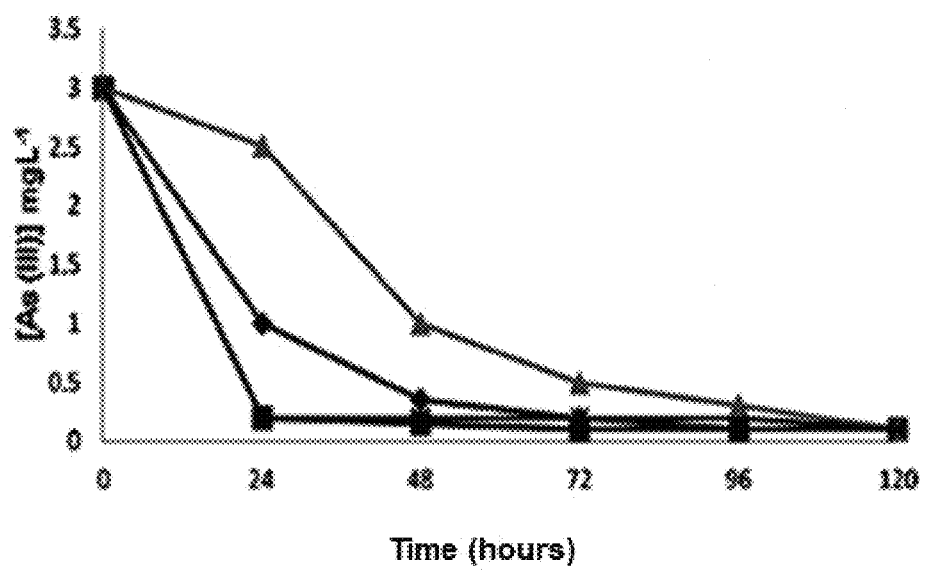
FIG. 8: It shows bioremediation of Arsenic (III) with *Pseudomonas aeruginosa* CSMY-1 in biofilms with and without glucose. Concentration of As (III) is 3 mg/L and varies with and without glucose at pH 6.5 and 7.0. (*) with glucose pH 6.5 (this curve practically overlaps with the curve with glucose pH 7.0); (▲) without glucose pH 6.5; (■) with glucose pH 7.0; (♦) without glucose pH 7.0.

In the case of the treatment without addition of trace metals, the biofilm bacteria removed 100% of the lowest concentrations of arsenic (0.05 and 0.1 mg/L) at 24 h and 100% of 1 mg/L of arsenic at 48 h. This strain removed 67% of arsenic at 48 h for the highest concentrations 2 and 3 mg/L. Trace metals were added at 24 h of incubation to improve arsenic removal at the highest concentration (3 mg/L), achieving 92% removal at 48 h and 100% at 96 h (FIG. 7). Starting from an initial concentration of 3 mg/L As (III) and adding glucose at 72 hours, 100% of arsenic is removed (FIG. 8).

Example 5

Figure 9:
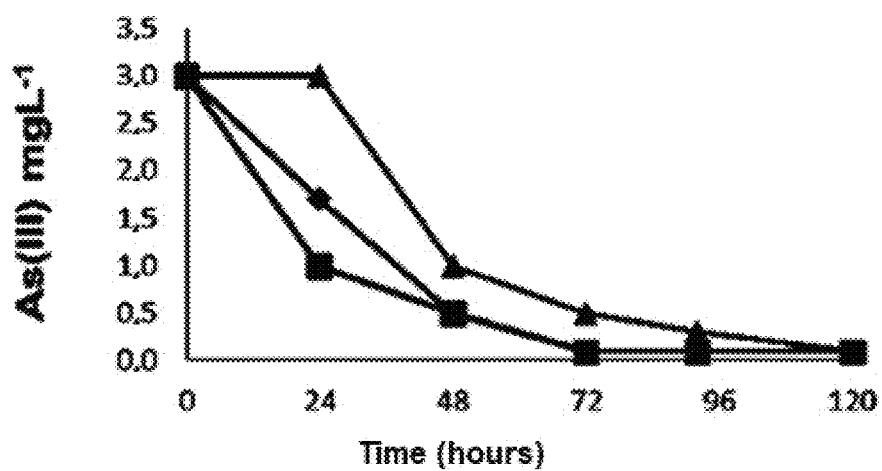
FIG. 9: It shows removal of arsenic (III) with biofilms of *Pseudomonas aeruginosa* CSMY-1 in an iron (II)-enriched medium. (■) Corresponds to addition of 0.1 mg/L Fe (II). (♦) Corresponds to addition of 0.05 mg/L Fe (II). (▲) Corresponds to liquid industrial waste with As (III) with biofilm without trace metals.

Removal of Arsenic (III) with *Pseudomonas aeruginosa* CSMY-1 in Biofilm Form in an Iron (II)-Enriched Medium Arsenic (III) removal was studied using iron (II)-enriched *Pseudomonas aeruginosa* CSMY-1 biofilms. Biofilms were formed by setting the bacteria in an Erlenmeyer flask with polyethylene strips and trypticase soy broth for 15 days in an incubator at 37° C. The toxicity of As (III) before and after the treatment was evaluated through a chronic bioassay with microalga *Selenastrum* sp. It was observed that when starting from an initial concentration of 3 mg/L As (III) at pH 6.5 and adding 0.05 and 0.1 mg/L of $Fe^{2+}$ as a degradation catalyst, 67% of arsenic was reduced at 24 h and 100% at 70 h (FIG. 9).

Example 6

Study of Ability of *Pseudomonas aeruginosa* CSMY-1 Biofilms in a Trace Metal-Enriched Medium to Remove Textile Dyes and Petroleum Hydrocarbons in Soil Removal of Textile Dyes Variables pH, Reactive black textile dye 5 (NR-5) concentration, and trace metal concentration were studied. The study was carried out at pH 7, 100 mg/L of dye to be degraded and 10 μL of trace metals. *Pseudomonas aeruginosa* CSMY-1 bacteria were incubated at 37° C. for 5 days to form biofilms and then inoculated under the abovementioned pollution conditions.

Figure 10:
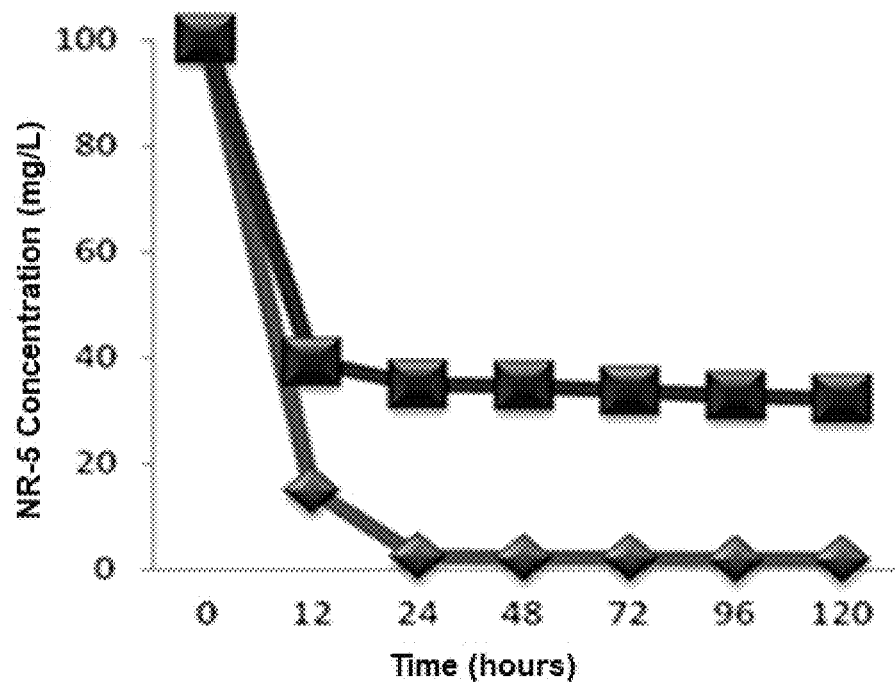
FIG. 10: It shows removal of NR-5 (100 mg/L) concentration in the presence (♦) and absence of trace metals (■).

Dye removal was monitored for 5 days by UV/visible spectrophotometry at 594 nm, achieving a 100% removal at 24 h in the treatment with trace metals at pH 7.0, and 67.68% for control treatment (only biofilm, without trace metals). At the end of the incubation period the nitrate concentration as a NR-5 oxidation product was measured, obtaining values of 3.6 and 2.1 mg/L for treatment without trace metals, respectively (FIG. 10). At the same time, the total organic carbon was reduced by 63.6%, showing that the bacteria are incorporating the compound as a carbon source to mineralize the same. This procedure demonstrates its efficiency since conventional textile dye removal treatments obtain similar results at 14 days, however in the present invention the same results are achieved in 120 hours.

Biofilm bacteria are also capable of decolorizing and degrading red dyes Drimaren K4-BL (RD K4-BL) and Cibacron Brilliant Yellow 3G-P (CBY 3G-P) in the presence of 100 μL of a trace metal solution containing Co, Ni, Mg, Fe.

Figure 11:
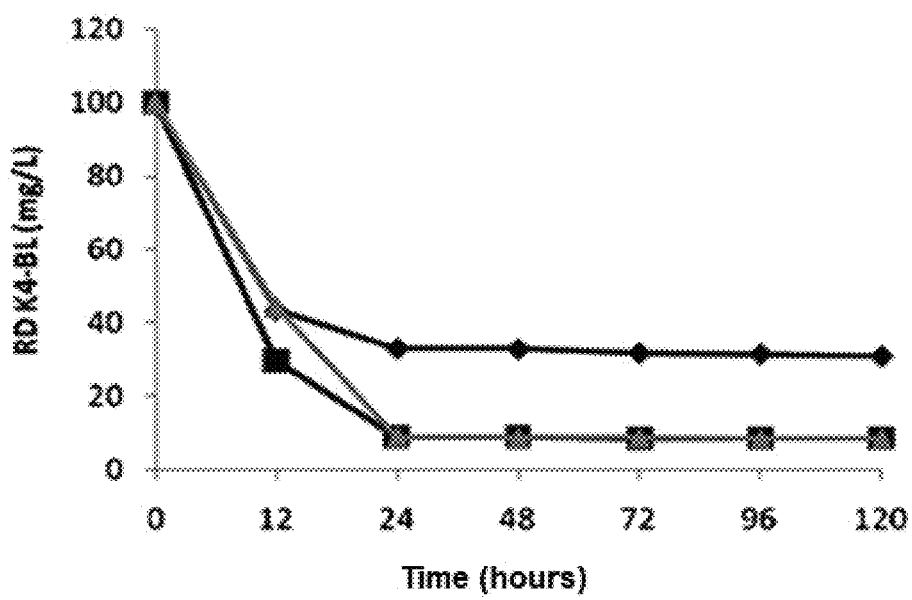
FIG. 11: It shows removal of RD K4-BL (100 mg/L) concentration in the presence and absence of trace metals. (♦) Corresponds to the control only with biofilm, that is, in the absence of trace metals. (■) Corresponds to treatment with biofilm and trace metals at 0 hours. (▲) Corresponds to treatment with biofilm and trace metals at 0 hours and 48 hours.
Figure 12:
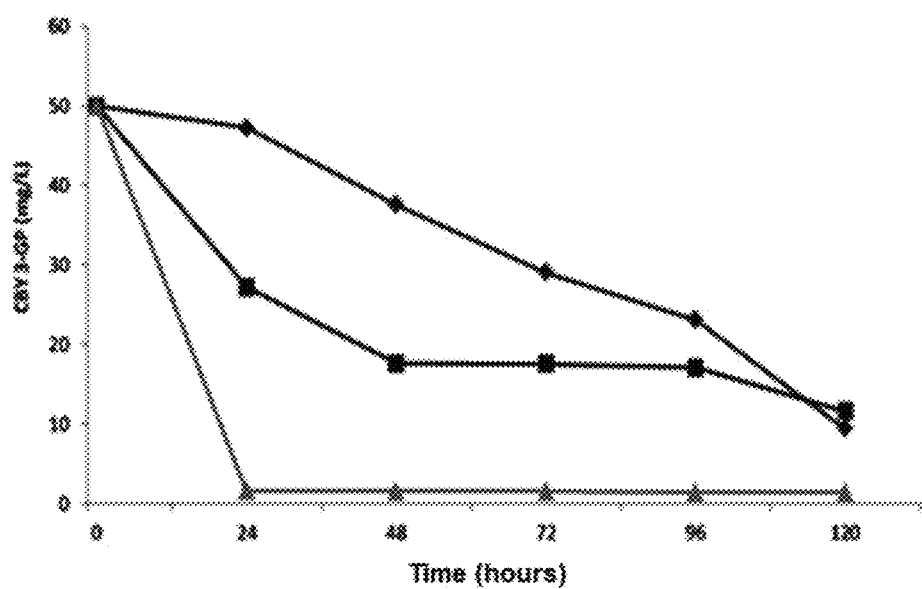
FIG. 12: It shows removal of CBY 3-GP (50 mg/L) concentration in the presence and absence of trace metals. (♦) Corresponds to control only with biofilm, that is, in the absence of trace metals. (■) Corresponds to treatment with biofilm and trace metals at 0 hours. (▲) Corresponds to treatment with biofilm and trace metals at 0 hours and 48 hours.

Degradation of these dyes was carried out at pH 7, 100 mg/L of RD K4-BL and 10 μL of trace metals. Removal kinetics was carried out during 120 hours, wherein the treatment comprising adding trace metal at 0 and 48 hours resulted in the highest removals for RD K4-BL and CBY 3G-P, 91.6% and 97.2% respectively (FIG. 11). Using this treatment, COD was reduced 66.27%, TOC was reduced 43% and 16% of nitrogen was mineralized to NO3- for dye RD K4-BL. COD was reduced 67.16%, TOC was reduced 48% and 58.3% of nitrogen was mineralized to nitrate for CBY 3G-P (FIG. 12).

Petroleum Hydrocarbons in Soil

Soil samples contaminated with petroleum hydrocarbons were evaluated and the capacity of *Pseudomonas aeruginosa* CSMY-1, in biofilms and pelagic (not biofilm) form, to degrade hydrocarbons was measured. To this end, the physical and chemical characteristics of the soil such as humidity, pH, electrical conductivity, and organic matter were measured, and remaining hydrocarbon concentration and toxicity were evaluated by *Selenastrum capricornutum, Daphnia magna, Eisenia foetida* and *Lactuca sativas*. The obtained results indicate that there is no significant difference between hydrocarbon removal using *Pseudomonas aeruginosa* CSMY-1 in biofilm compared to using the bacteria in pelagic form, since in both cases 99.9% of hydrocarbons present in soil samples were degraded. After the treatment, the toxicity test with *Daphnia magna* showed that *Pseudomonas aeruginosa* CSMY-1 in biofilm was able to decrease mortality by about 80%, contrary to the pelagic bacteria where mortality was only reduced by 50%. In the case of *Daphnia magna* species, ANOVA analysis showed significant differences between the hydrocarbon samples and the control samples before and after bacteria treatment, unlike *Lactuca sativas* and *Selenastrum capricornutum*, wherein ANOVA analysis did not show significant differences between contaminated samples and control sample before and after treatment. Soil bioremediation process removed 93% of PHCs (petroleum hydrocarbons) using *Pseudomonas aeruginosa* CSMY-1 in pelagic form and 94% and 99% using *Pseudomonas aeruginosa* CSMY-1 in biofilm. The removal of n-alkanes was 100% in both cases.

The invention claimed is:

1. A method for bioremediation of pollutants from a contaminated environment, said method comprising:

a. growing bacterium *Pseudomonas aeruginosa* deposited in the Microbial Genetic Resources Bank of the Chilean Collection of Microbial Genetic Resources (CChRGM) under accession number RGM2262, having greater efficiency of removal of different types of pollutants grown in a medium with a trace metal solution;

b. incubating said bacterium *Pseudomonas aeruginosa*, accession number RGM2262, together with a polyethylene sheet in the medium to form a biofilm during a period of time from 5 to 10 days, from 20° C.-40° C. at a pH range from 4 to 11 to allow the removal of pollutants; and c. exposing said biofilm to contaminated soils or liquid industrial waste from textile industry, cellulose industry, petroleum industry or other industry containing arsenic, wherein in a maximum of 5 days, the *Pseudomonas aeruginosa*, accession number RGM2262, removes over 90% of pollutants in said contaminated soils or liquid of industrial waste.

2. The method for bioremediation according to claim 1, wherein the strain has an increased activity for removal of pollutants from industrial effluents, which contain cellulose, Kraft lignin, textile compounds, dyes, phenols, arsenic (III), hydrocarbons and petroleum derivatives.

3. The method for bioremediation according to claim 1, wherein for biofilm formation, bacterium *Pseudomonas aeruginosa* RGM2262 is incubated in a culture medium at an initial concentration of from 0.01 to 10 g/L of the strain together with the polyethylene sheet, for a period of time from 3 to 15 days at a temperature from 25° C. to 40° C.

4. The method for bioremediation according to claim 1, wherein pollutants removed by bacterium *Pseudomonas aeruginosa* RGM2262 in biofilm form are pollutants from the textile industry, which contain dyes selected from the group consisting of Reactive Black 5, Drimarene Color Red K4BL (RD K4-BL) and Cibacron Brilliant Yellow 3G-P (CBY 3G-P).

5. The method for bioremediation according to claim 1, wherein pollutants removed by bacterium *Pseudomonas aeruginosa* RGM2262 in biofilm form are pollutants from cellulose industry which contain lignin in the waste.

6. The method for bioremediation according to claim 1, wherein pollutants removed by bacterium *Pseudomonas aeruginosa* RGM2262 in biofilm form are pollutants from petroleum industry with petroleum waste and their derivatives.

7. The method for bioremediation according to claim 1, wherein pollutants removed by bacterium *Pseudomonas aeruginosa* RGM2262 in biofilm form are arsenic (III)-containing waste.

8. The method for bioremediation of claim 1, wherein the method further comprises adding glucose at a concentration from 0.1 to 0.5 mg/L.

9. The method for bioremediation according to claim 1, wherein the trace metals used are Co, Ni, Mg, Fe at a volume from 10 to 200 µL.

10. The method for bioremediation of claim 1, wherein the method further comprises adding iron at a concentration from 0.05 to 0.1 mg/L.

\* \* \* \* \*